United States Patent [19]

Christena

[11] 4,016,047
[45] Apr. 5, 1977

[54] SEPARATION AND RECOVERY OF POLYCHLORINATED PHENOLS

[75] Inventor: Ray C. Christena, Wichita, Kans.

[73] Assignee: Vulcan Materials Company, Birmingham, Ala.

[22] Filed: Mar. 21, 1975

[21] Appl. No.: 560,800

Related U.S. Application Data

[63] Continuation of Ser. No. 414,533, Nov. 9, 1973, Pat. No. 3,909,365.

[52] U.S. Cl. .................................... 203/6; 203/38; 203/91; 260/623 H
[51] Int. Cl.² ........................................ C07C 39/36
[58] Field of Search ............. 203/6, 29, 38, 91, 32; 260/623 R, 623 H

[56] References Cited

UNITED STATES PATENTS

| | | | |
|---|---|---|---|
| 3,403,186 | 9/1968 | Schlichting et al. | 260/623 R |
| 3,454,654 | 7/1969 | Hobbs | 260/623 H |
| 3,770,835 | 11/1973 | Garabedian | 260/623 R |
| 3,852,160 | 12/1974 | Watson et al. | 203/6 |
| 3,852,161 | 12/1974 | Yoshimme et al. | 203/6 |
| 3,909,365 | 9/1975 | Christena | 203/6 |

OTHER PUBLICATIONS

Biltz et al., Berichte 37 4017, 4018 (1904).

*Primary Examiner*—Wilbur L. Bascomb, Jr.
*Attorney, Agent, or Firm*—Burns, Doane, Swecker & Mathis

[57] ABSTRACT

Polychlorinated phenols (e.g., pentachlorophenol) of improved color are made by vacuum distilling polychlorinated phenols containing dark color-forming impurities in the presence of a color inhibitor such as free radical-acting substances (e.g., free radical-acting compounds of the phenol, hydroquinone, organic sulfur derivative, organic phosphite, amine and aldehyde type). In addition, the chlorodioxin content of the impure pentachlorophenol (generally about) 2,000 p.p.m.) is reduced to a residual chlorodioxin content of less than 25 p.p.m. during distillation.

5 Claims, No Drawings

SEPARATION AND RECOVERY OF POLYCHLORINATED PHENOLS

This is a continuation of application Ser. No. 414,533, filed Nov. 9, 1973, and now U.S. Pat. No. 3,909,365.

BACKGROUND OF THE INVENTION

For some time it has been recognized that phenol, especially when produced by the cumene process or by sulfonation of benzene, inherently contains some impurities which upon chlorination of the phenol give rise to objectionable color formation. See, for example. U.S. Pat. No. 2,864,869. Such impurities are present even in phenol which is U.S.P. grade, and are thought not to be separable from the phenol by ordinary fractional distillation. See, U.S. Pat. No. 3,029,292. Hence, a number of techniques have been developed for the purification of phenol which involve contacting the phenol with some chemical agent or heat treating it in the presence of a catalyst and thereafter recovering the phenol by fractional distillation. See, for example, U.S. Pat. Nos. 3,102,149 and 3,029,293 as well as those patents mentioned above. Upon subsequent chlorination, phenols treated in such a manner show a reduction in the typical dark reddish or brownish color which chlorination usually imparts to pentachlorophenol made from phenols produced by the cumene process or sulfonation of benzene.

However, such phenol purification techniques suffer from the disadvantages of elaborate and costly equipment and procedure. In other words, in order to obtain polychlorinated phenol such as pentachlorophenol free from colored impurities, heretofore it was necessary to perform a special purification on phenol already purified to U.S.P. grade, recover the phenol from such a special process, chlorinate the phenol and then recover the chlorinated phenol.

An improved process for the manufacture of polychlorinated phenols of improved (i.e., lighter) color is disclosed in a copending U.S. patent application assigned to the assignee of the present invention. As therein disclosed, chlorination of the phenol starting material is performed to obtain a mixture of chlorophenols containing from 1 to 3 chlorine atoms per molecule to phenol, at least 40% of the chlorinated phenol mixture being in the form of dichlorophenols. The reaction mixture is thereafter distilled to separate a light colored chlorophenol distillate from a residue containing dark color-forming impurities, and the distillate may be further chlorinated to form pentachlorophenol.

Certain impurities such as the chlorodibenzo-p-dioxins (commonly known as chlorodioxins) generally present in chlorinated phenols may be toxic to humans, possibly even in the low concentrations, e.g., about 2,000 p.p.m., present in technical grade pentachlorophenol. These chlorodioxin impurities are apparently formed during phenol chlorination and are thus not removed during special phenol purification procedures prior to chlorination. If the safety hazard of these compounds is established, then the removal of chlorodioxin to a safe level (i.e., below about 100 p.p.m.) will be necessary.

OBJECTS AND SUMMARY OF THE INVENTION

It is an object of the present invention to produce chlorinated phenols of light color by a process which obviates or substantially alleviates the problems and drawbacks associated with prior art techniques.

It is another object of the present invention to produce essentially color-free polychlorinated phenols such as pentachlorophenol without any elaborate purification of the phenol.

Still another object is to reduce the chlorodioxin content of pentachlorophenol while also removing color-producing impurities.

These and other objects as well as the manner of achieving them will become apparent to those skilled in the art from the detailed description which follows.

The present invention provides a method for the separation and recovery of polychlorinated phenol from dark color-forming impurities contained therein comprising the steps of:

a. introducing into a distilland mixture of at least one polyclorinated phenol and dark color-forming impurities, an amount effective to inhibit color formation of at least one color inhibitor selected from the group consisting of zinc dust and free radial-acting substances;

b. distilling the resulting color inhibitor containing distilland to separate polychlorinated phenol vapors therefrom; and c. condensing said vapor to recover purified polychlorinated phenols.

In the absence of a contrary indication, all proportions and percentages of materials are expressed in this specification on a weight basis.

DESCRIPTION OF PREFERRED EMBODIMENTS

Although the process of the present invention may advantageously be performed on any chlorinated phenol, regardless of the method of manufacturing the chlorinated phenol, it has been found that the present process is particularly applicable to the removal of dark color-forming impurities from pentachlorophenol.

The pentachlorophenol which may be treated according to the present invention may be produced in any suitable manner. Generally, pentachlorophenol is produced by the chlorination of phenol or by hydrolysis of hexachlorobenzene. Although either method is acceptable and both methods are known in the art, production of pentachlorophenol by the chlorination of phenol is preferred.

The phenol starting material, which may be chlorinated to form the chlorinated phenols, may be produced by the decomposition of cumene hydroperoxide of by sulfonation of benzene. Even when purified to a degree which satisfies U.S.P. requirements, such phenol still contains traces of color-forming impurities which cannot be separated by distillation or other conventional methods Chlorinated phenols derived from phenol made by the above mentioned processes are significantly improved in color by the process of the present invention.

When cumene process phenol is used as the starting material, it is preferred to use the phenol after it has been treated, for example, by fractional distillation of the washed and neutralized cumene hydroperoxide decomposition reaction product. Such a treatment removes most of the lower boiling material such as acetone, cumene, alpha-methylstyrene and most of the higher boiling materials such as acetophenone and phenyl dimethylcarbinol, although a residual quantity, e.g., up to about 0.1 percent based on phenol, of any or all of these impurities may remain in the phenol fraction.

Chlorination may be conducted in any convenient manner known. Chlorination processes are shown, for example, in U.S. Pat. Nos. 2,131,259 and 2,947,790, the specifications of which are both herein incorporated by reference.

Typically, in these known processes, the phenol starting material is reacted at a temperature at the start of the chlorination in the range of 65° to 130° C. (preferably about 100° to 110° C) and is held at this temperature until the melting point of the product is 95° C, and about 3 to 4 atoms of chlorine are combined as determined by analysis, at which time the temperature is progressively increased to maintain a preferred differential temperature of 10° C. over the product melting point.

The chlorination process is carried out at substantially atmospheric pressure for a time of from about 5 to about 15 hours. The chlorination reaction may be carried out in the liquid phase in the absence of any added solvents and in the presence of aluminum chloride catalyst. The catalyst concentration in these known chlorination processes is maintained below 0.0085 mol of anhydrous aluminum chloride per mol of phenol, preferably not more than 0.075 mol and not less the 0.004 mol of anhydrous aluminum chloride per mol of phenol. The initial chlorination up to where 2 to 2.7 atoms of chlorine are combined per mol of phenol may be carried out in the absence of catalyst.

Pentachlorophenol production by hydrolysis of hexachlorobenzene is also well-known and is shown, for example, in U.S. Pat. Nos. 2,107,650 and 2,812,366.

An efficacious chlorination process for the production of pentachlorophenol is disclosed in the aforementioned copending U.S. patent application which discloses chlorination of the phenol starting material to obtain a mixture of chlorophenols containing from 1 to 3 chlorine atoms per molecule of phenol, at least 40% of the chlorinated phenol mixture being in the form of dichlorophenols. The reaction mixture is thereafter distilled to separate a light-colored chlorophenol distillate from a residue containing dark color-forming impurities, and the distillate may be further chlorinated to form pentachlorophenol.

Generally, all of the above noted processes yield "technical grade" pentachlorophenol. In addition, and regardless of the method of production, technical grade pentachlorophenol is a commercially available product. Technical grade pentachlorophenol is a generally brownish-colored solid which contains from about 86 to 95 percent pentachlorophenol, about 2 to 10 percent tetrachlorophenol and up to about 4 percent of other compounds, most of which are unidentified. As noted before, technical grade pentachorophenol generally also contains about 1800 to 2400, generally about 2,000 parts per million (p.p.m.) of chlorodioxin (e.g., chlorodibenzo-p-dioxins) determined as octachlorodibenzo-p-dioxin. Although special distillation techniques have been performed on phenol to lessen the dark coloration of the resulting chlorinated phenols, such techniques do not appear to affect the chlorodioxin content of the product.

Purification of the pentachlorophenol containing dark color-forming impurities and chlorodioxin impurities may be conducted by distilling such impurity-containing pentachlorophenol in the presence of an amount effective to inhibit color formation of at least one color inhibitor selected from the group consisting of zinc dust and free radical-acting substances to separate pentachlorophenol vapor therefrom and condensing said vapor to recover purified pentachlorophenol. Ethylene thiourea or zinc dust appear to offer an optimum combination of improved product color, process efficiency and cost and are therefore the preferred color inhibitors.

The free radical-acting color inhibitors can be and free radical-acting substances which provide improved color properties and remove color-forming impurities from the pentachlorophenol during distillation. Typically, suitable free radical-acting color inhibitors include free radical-acting compounds of the phenol, hydroquinone, organic sulfur derivative, organic phosphite, amine or aldehyde type.

Phenol compounds, for example, which have been found suitable for use in the present invention include 2,6-ditertiary butyl cresol, alpha naphthol, p-aminophenol, 4-(methylthio)phenol, 2,2'-methylenebis(4-methyl-6-tert-butyl phenol), Plastanox 1161, a hindered phenol commercially available from the American Cyanamid Co., 2,2'-methylenebis (4-ethyl-6-tetbutyl phenol) and p-tertiary butyl catechol.

Suitable hydroquinone compounds include hydroquinone, 2,5-ditertiary butyl hydroquinone, monotertiary butyl hydroquinone and monomethyl ether of hydroquinone.

Organic sulfur derivatives which have been found suitable include alkyl phenol disulfide commercially available as Vultac No. 3 from the Pennwalt Company; ethylene thiourea, mixed thioureas commercially available as Pennzone L from the Pennwalt Company; liquid dithiocarbamate commercially available as Merac No. 255 from the Pennwalt Company; ditridecylthiodipropionate, and distearylthiodipropionate.

Suitable organic phosphites include trinonyl phosphite, tris-2 (chloroethyl)-phosphite, and triisooctyl phosphite.

Amines which have been found suitable include N,N'-bis(1,4-dimethylpentyl)-p-phenylene diamine.

The color inhibitor is added to the impurity-containing pentachlorophenol in an amount effective to inhibit color formation, which amount is generally in the range of from about 0.02 to about 2, preferably from about 0.1 to about 0.5 percent by weight of the starting material.

The term "free radical-acting substance" is intended to include those compounds such as described above which function as scavengers for the impurities in the polychlorinated phenol.

Although the mechanisms of reaction are unclear and I do not wish to be bound by theoretical considerations, it would appear that the color inhibitors react with the color-imparting impurities in the crude pentachlorophenol to render them separable on distillation.

A conventional vacuum flask evaporator is satisfactory to carry out the distillation. For example, the distillation apparatus may be a vacuum batch still with heat being supplied to the still by a forced circulation reboiler heated with circulating hot oil. Vapors pass out the top of the batch pot through a column containing side-to-side trays and are condensed in a shell and tube type condenser (vapor on the inside of the tubes and high pressure steam generated on the outside). A reduced pressure is maintained on the system by a dual stage jet ejector in manner well known in the art.

Typically, the distillation is preformed under vacuum conditions, e.g., at a pressure of above 30 up to about 160 or more mm. Hg, preferably from about 35 to about 150 mm. Hg, and at a temperature of from about 185° to 235° C., preferably from about 195° to about 220° C. Distillation may be continued to achieve from about 84 percent to 96 percent, often from about 90 percent to 96 percent, distillate recovery with good results.

When the distillation is carried out under the conditions noted above, the distillate comes over essentially water-white in color, while the residue remains as a dark liquid. That is, a 10 weight percent sample of the distillate in xylene generally yields a transmission value using a light having a wavelength of 475 m$\mu$ and a light path of 10 mm. of from about 95 to about 100 percent of the value of a water-white xylene reference standard. The chlorodioxin content of the essentially water-white colored distillate is generally below about 25 p.p.m.

Pentachlorophenol is used in the preservation and treatment of wood In certain applications (fence poles, housing substructures), pentachlorophenol color is relatively unimportant. In many other uses in the wood-working industry, particularly where painting of the treated product is necessary, a light or water-white colored pentachlorophenol is highly desirable.

The invention is additionally illustrated in connection with the following examples which are to be considered as illustrative of the present invention. It should be understood, however, that the invention is not limited to the specific details of the Examples.

EXAMPLE 1

Distilled pentachlorphenol was obtained from equipment of two sizes. The smaller reactor consisted of a glass tube in a temperature controlled aluminum block. A charge of 5 parts by weight impure pentachlorophenol was placed in a heated zone and distilled or sublimed into a cool zone outside the block. The reactor was equipped with a temperature controlled, manostat, traps and vacuum gauge and pump. The larger reactor contained a 500 parts by weight impure pentachlorophenol charge in a semi-spherical glass vessel equipped with a short Vigreaux tube, condenser, receiver, and the usual vacuum equipment as with the smaller reactor. The reactor was heated by a molten salt bath.

The starting material for each run was commercially available technical grade pentachlorophenol. This material was a dark brown-colored solid having a composition of about 94 percent pentachlorophenol, 2 percent tetrachlorophenol, 2000 p.p.m. chlorodioxin (determined as octachlorodibenzo-p-dioxin), balance not identified.

In each run, the indicated amounts of impure pentachlorophenol and color inhibitor are charged to the reactor and the mixed charge heated to the indicated temperature under the indicated pressue. Color of the resulting distillate is determined visually and by measuring the transmittance of a light 475 m$\mu$ through a 1 cm. Pyrex glass cell with a light path of 10 mm. containing 10 weight percent of pentachlorophenol product in xylene. A matching cell of the water-white xylene is used as a reference standard and is assigned a value of 100% transmission.

The run conditions utilized and results obtained are shown below in Table I.

Table 1

| Color Inhibitor Type | Run Conditions | | | | | Results | | | Comments |
|---|---|---|---|---|---|---|---|---|---|
| | Sample Size Parts by Weight | Color Inhibitor, % | Pressure, mm Hg | Temperature. °C. | % of Charge Distilled | Chlorodibenzo-p-dioxins, ppm | Transmittance, % | Visual Color of Solid | |
| Control - distilled - no inhibitor | 500 | none | 150 | 246 | 85.6 | 91 | 90.2 | yellow | |
| " | 500 | " | 134 | 244 | 92.6 | 61 | 91.4 | " | |
| " | 500 | " | 51 | 213 | — | <25 | 86.4 | " | |
| Phenols - hydroquinones | | | | | | | | | |
| 2,6-Ditertiary butyl cresol (Shell Ionol)$^b$ | 500 | 0.2 | 51 | 214 | — | ND* | 96.5 | white | |
| " | 5 | 0.1 | 36 | 198 | — | — | 100.0 | " | |
| 2,5-Ditertiary butyl hydroquinone | 500 | 1.0 | 125 | 235 | — | ND | 97.2 | " | |
| " | 5 | 1.0 | 36 | 198 | — | — | 98.5 | " | |
| Hydroquinone | 5 | 0.1 | 35 | 198 | — | 16 | 98.7 | " | |
| Monotertiary butylhydroquinone | 5 | 1.0 | 35 | 198 | — | — | 99.5 | " | |
| Alpha Naphthol | 5 | 0.1 | 36 | 198 | — | — | 100.0 | " | |
| p-Aminophenol | 5 | 1.0 | 36 | 198 | — | — | 53.0 | " | |
| 4-(Methylthio)phenol | 5 | 1.0 | 36 | 198 | — | — | 100.0 | " | |
| Monomethyl ether of hydroquinone | 5 | 1.0 | 36 | 198 | — | — | 100.0 | | |
| 2,2'-Methylene bis(4-methyl-6-tert-butyl phenol) [Plastanox 2246]$^c$ | 5 | 0.1 | 36 | 198 | — | — | 94.8 | " | |
| " | 500 | 0.25 | 47 | 215 | 92.0 | ND | 97.0 | " | |
| Hindered phenol [Plastanox 1161]$^c$ | 5 | 0.5 | 36 | 198 | — | — | 99.5 | " | |
| 2,2'-Methylene bis(4-ethyl-6-tert-butyl phenol) [Plastanox 425]$^c$ | 5 | 0.1 | 36 | 198 | — | — | 100.0 | " | |
| p-Tertiary butyl catechol | 5 | 0.1 | 36 | 198 | — | — | 98.8 | " | |
| Alkyl phenol disulfide [Vultac No. 3]$^c$ | 500 | 0.25 | 49 | 218 | — | ND | 98.0 | " | |
| Sulfur compounds | | | | | | | | | |
| Ethylene thiourea | 5 | 1.0 | 36 | 198 | — | — | 94.8 | white | |
| " | 500 | 0.2 | 50 | 214 | — | 30 | 97.9 | " | |
| Mixed thioureas (Pennzone L)$^c$ | 500 | 0.25 | 50 | 214 | — | ND | 96.0 | " | |
| Liquid dithiocarbamate (Merac No. 255)$^c$ | 500 | 0.25 | 48 | 214 | 92.0 | 100 | 90.2 | " | |
| Ditridecylthiodipropionate [Plastanox 711]$^c$ | 5 | 1.0 | 36 | 198 | — | — | 99.4 | " | |
| " | 500 | 0.1 | 50 | 215 | — | <25 | 98.0 | " | |

Table 1-continued

| Color Inhibitor Type | Run Conditions ||||| Results ||||
|---|---|---|---|---|---|---|---|---|
| | Sample Size Parts by Weight | Color Inhibitor, % | Pressure, mm Hg | Temperature, °C. | % of Charge Distilled | Chlorodibenzo-p-dioxins, ppm | Transmittance, % | Visual Color of Solid | Comments |
| Distearyl thiodipropionate [Plastanox STDP]$^c$ | 5 | 0.17 | 36 | 198 | — | — | 99.0 | " | |
| Alkyl phosphites | | | | | | | | | |
| Trinonyl phosphite (Uvi-Nox 3100)$^d$ | 5 | 1.0 | 36 | 198 | — | — | 99.0 | " | |
| " | 500 | 0.2 | 50 | 215 | 90.0 | ND | 98.8 | " | |
| Tris-2(chloroethyl)-phosphite | 500 | 0.5 | 110 | 237 | 74.4 | ND | 94.1 | " | |
| Triisooctyl phosphite | 5 | 1.0 | 36 | 198 | 89.4 | 23 | — | " | |
| | 500 | 1.0 | 65–150 | 180–231 | 92.6 | — | 97.0 | " | |
| Amines and Aldehydes, Acids -Miscellaneous | | | | | | | | | |
| N,N'-bis(1,4-dimethyl-pentyl)-p-phenylene diamine [Tenamine 4]$^f$ | 5 | 1.0 | 36 | 198 | — | — | 81.2 | " | Solution clear and lt. purple |
| " | 500 | 0.25 | 48 | 214 | 93.0 | ND | 98.5 | " | |
| Metals | | | | | | | | | |
| Zinc dust | 500 | 0.35 | 50 | 215 | 89.0 | <25 | 100.0 | " | |

* None detected
$^b$ Shell Chemical Corporation
$^c$ American Cyanamid Company
$^d$ GAF Corporation
$^e$ Pennwalt Corporation
$^f$ Eastman Chemical Products, Inc.

These runs show that various color inhibitor compounds in varying amounts are effective to remove all or substantially all of the dark color-forming impurities under vacuum distillation conditions. Color improvement was performed with the recovery of substantially all of the original charge. Both visual color and transmittance of the samples are very good (i.e., generally white color and 95% or better transmittance) regardless of sample size or amount of inhibitor. In addition, the amount of chlorodioxins is substantially reduced (i.e., below 25 p.p.m.). Apparently some of the p-aminophenol and N,N'-bis(1,4-dimethylpentyl)-p-phesodium borohydride run yielded good transmittance and visual color values, the "heels" or residue of undistilled charge was generally larger (and the percent of charge distilled was therefore generally smaller) than realized with the color inhibitors of the present invention. Other runs with sodium borohydride indicate that relatively large amounts of the material must be used to achieve acceptable color improvement. These runs also indicate, however, that the percent of charge distilled decreases with increasing amounts of sodium borohydride and that values of only about 75 to 80 percent of the charge distilled are often realized.

Table 2

| Color Inhibitor Type | Run Conditions ||||| Results ||||
|---|---|---|---|---|---|---|---|---|
| | Sample Size, Parts by Weight | Color Inhibitor, % | Pressure, mm Hg | Temperature, °C | % of Charge Distilled | Chlorodibenzo-p-dioxins, ppm | Transmittance, % | Visual Color of Solid | Comments |
| Amines and Aldehydes, Acids - Miscellaneous | | | | | | | | | |
| Dimethyl sulfoxide | 5 | 2.0 | 36 | 198 | — | — | 98.0 | lt. yellow | |
| Ethylene diamine tetra-acetic acid | 5 | 1.0 | 36 | 198 | — | — | 94.8 | " | |
| Oxalic acid | 5 | 1.0 | 36 | 198 | — | — | 83.2 | " | Solution contains suspended precipitate & is lt. yellow |
| Metals and Inorganic Compounds | | | | | | | | | |
| Iron powder | 5 | 1.0 | 36 | 198 | — | — | 94.2 | yellow | |
| Sodium meta bisulfite | 5 | 1.0 | 36 | 198 | — | — | 95.0 | " | |
| Stannous oxalate | 5 | 2.0 | 36 | 198 | — | — | 94.2 | " | |
| Sodium borohydride | 5 | 0.28 | 36 | 198 | 83.6 | — | 98.7 | white | | nylene diamine color inhibitors distilled over during the run which caused the transmittance of the resulting distillate samples to be below that obtained with the other color inhibitor materials.

COMPARATIVE EXAMPLE

Example I is repeated utilizing dimethyl sulfoxide, ethylene diamine tetraacetic acid, oxalic acid, iron powder, sodium meta bisulfite, sodium borohydride and stannous oxalate. The conditions and results obtained are shown below in Table II. Generally, the pentachlorophenol distilled containing these compounds had unsatisfactory color (yellow). While the The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. A method for the separation and recovery of polychlorinated phenols from dark color-forming impurities contained therein comprising the steps of: (a) introducing into a distilland mixture of at least one polychlorinated phenol and dark color-forming impurities, an amount effective to inhibit color formation of at least one color inhibitor selected from the group consisting of; a phenol derivative selected from the group consisting of 2,6-ditertiary butyl cresol, alpha naphthol, p-aminophenol 4-(methylthio) phenol, 2,2'-methylenebis (4-methyl-6-tertbutyl phenol), 2,2'-methylenebis (4-ethyl-6-tertbutyl phenol), and p-tertiary butyl catechol a hydroquinone compound selected from the group consisting of hydroquinone, 2,5-ditertiary butyl hydroquinone, monotertiary butyl hydroquinone, and the monomethyl ether of hydroquinone; an organic sulfur compound selected from the group consisting of alkyl phenol disulfide, liquid thiocarbamate, ditridecylthiodipropionate, and distearylthiodipropionate; and an organic phosphite compound selected from the group consisting of trinonyl phosphite, tris-2(chloroethyl)-phosphite, and triisooctyl phosphite, (b) distilling the resulting color inhibitor containing distilland to separate polychlorinated phenol vapors therefrom; and (c) condensing said vapor to recover purified polychlorinated phenols in an amount of at least about 84 percent of the impurity-containing polychlorinated phenol.

2. The method of claim 1 in which the said color inhibitor is present in the mixture in an amount of from about 0.02 percent to about 2 percent by weight of the mixture.

3. The method of claim 2 in which said distillation is performed at a pressure of above about 30 mm. Hg.

4. The method of claim 1 in which the distillation is performed at a temperature of above about 185° C.

5. A method for the separation and recovery of pentachlorophenol from dark color-forming impurities contained therein comprising the steps of: (a) introducing into a distilland mixture of pentachlorophenol and dark color-forming impurities, an amount effective to inhibit color formation of at least one color inhibitor selected from the group consisting of a phenol derivative selected from the group consisting of 2,6-ditertiary butyl cresol, alpha naphthol, p-aminophenol, 4-(methylthio) phenol, 2,2'-methylenebis (4-methyl-6-tertbutyl phenol), 2,2'-methylenebis (4-ethyl-6-tertbutyl phenol), and p-tertiary butyl catechol; a hydroquinone compound selected from the group consisting of hydroquinone 2,5-ditertiary butyl hydroquinone, monotertiary butyl hydroquinone, and the monomethyl ether of hydroquinone; an organic sulfur compound selected from the group consisting of alkyl phenol disulfide, liquid thiocarbamate, ditricedylthiodipropionate, and distearylthiodipropionate; and an organic phosphite compound selected from the group consisting of trinonyl phosphite, tris-2(chloroethyl)-phosphite, and triisooctyl phosphite; (b) distilling the resulting color inhibitor containing distilland at a pressure of above about 30 mm. Hg and a temperature above about 185° C to separate pentachlorophenol vapors therefrom; and (c) condensing said vapor to recover purified pentachlorophenol in an amount of at least about 84 percent of the impurity-containing penthachlorpheol.

* * * * *